July 30, 1968 C. F. ZAIGER Plant Pat. 2,822
APRICOT TREE
Filed Sept. 21, 1966
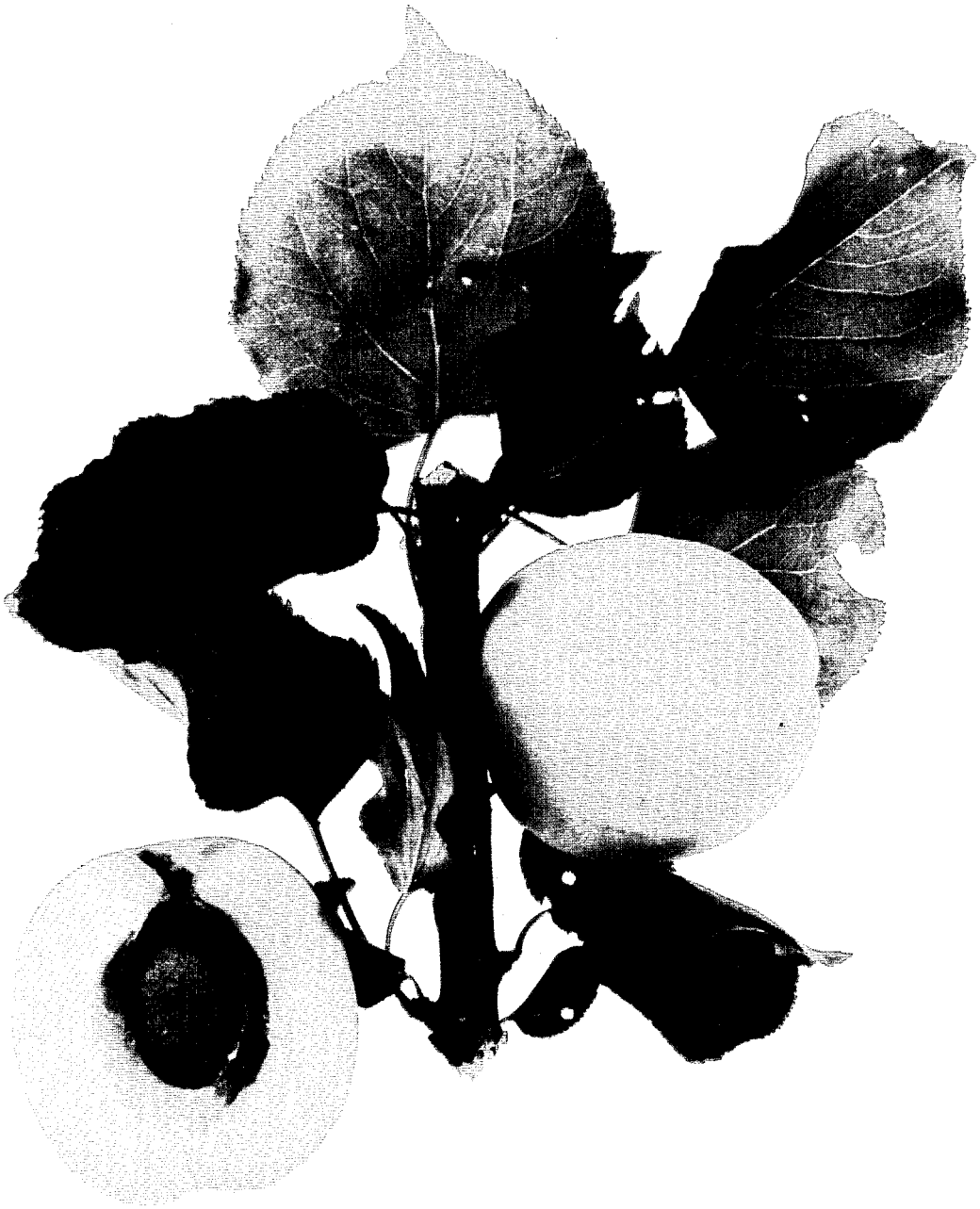
INVENTOR
C. Floyd Zaiger United States Patent Office Plant Pat. 2,822
Patented July 30, 1968

2,822
APRICOT TREE

Chris Floyd Zaiger, 537 Rosemore Ave.,
Modesto, Calif. 95351

Filed Sept. 21, 1966, Ser. No. 581,425
1 Claim. (Cl. Pit.—39)

My present invention relates to a new and distinct variety of apricot tree. Its novelty consists of the following unique combination of features which are outstanding in the new variety:

(1) A high degree of desirable red skin color on the side of the fruit which is exposed to the sun;

(2) The large size of the fruit;

(3) The extreme firmness of the fruit and its good shipping characteristics;

(4) Coloring of the fruit two to four weeks before ripening;

(5) The early ripening period of the fruit, occurring in late May.

My new variety originated as a first generation seedling selection from a group of Perfection apricot (nonpatented) seedlings grown by me on my property in Modesto, Calif. The pollen parent was of unknown origin.

In comparison with its seed parent, my new variety bears large to extra large fruit; is much firmer when ripe, giving it greater shipping quality; has a higher degree of red skin color, and ripens approximately 15 to 25 days earlier.

The foregoing characteristics and distinctions definitely differentiate my new variety from its seed parent as well as from all other varieties of which I am aware, and asexual reproduction of the new variety by budding and grafting, as performed at Modesto, Calif., show that said characteristics come true to form and are established and transmitted through succeeding propagations.

The accompanying photographs show typical specimen of the foliage and fruit of my new variety, with upper and lower surfaces of the foliage being illustrated and exterior and sectional view of the fruit being shown. These illustrations were taken shortly after being picked at maturity (shipping ripe). The colors are as nearly true as is reasonably possible in a color representation of this type.

The following is a detailed description of the foliage and fruit of my new variety, as based upon observations of specimens grown at Modesto, Calif., with color terminology in accordance with Reinhold Color Atlas by A. Kornerup and J. H. Wanscher.

Date of first and last picking: Generally ripens in late May, although over prolonged observations, dates of first ripening varied from May 20 to May 25, with last picking from June 1 to June 8.

Tree:
- *Size.*—Large.
- *Figure.*—Usual.
- *Shape.*—Usual.
- *Productivity.*—Heavy to medium.

Branches:
- *Size.*—Vigorous, stock to medium caliper in relation to length, from smooth to medium roughness.
- *Color.*—Reddish-brown, Plate BF7 to photo brown, Plate 9E8.
- *Lenticels.*—Present.

Leaves:
- *Size.*—Large.
- *Average length.*—Three inches to three and three-quarters.
- *Average width.*—Two and three-quarter inches to three and one-half inches.
- *Shape.*—Ovate to orbicular, pointed.
- *Petiole.*—Length average.
- *Glands.*—Two or more.
- *Color.*—Upper surface dark green, Plate 27F5 to dull green, Plate 27E4.

Flower buds:
- *Size.*—Medium to small.
- *Shape.*—Medium to short, plump.

Flowers:
- *Dates of blooms.*—Feb. 23, 1966, to Mar. 10, 1966. Varies from year to year due to weather variations.
- *Size.*—Medium to large.
- *Color.*—White, faint tinge of pink.

Fruit: Shipping ripe—the last week of May; eating ripe—the first week of June.
- *Size.*—Slightly variable; large, axial diameter from one and three-quarter inches to two and one-half inches. Transverse diameter in suture plane—from two and one-quarter inches to two and three-quarter inches. Diameter measured at right angles to suture plane—from one and five-eighths to two and three-eighths.
- *Form.*—Slightly variable, symmetrical, globose, at times somewhat compressed laterally toward suture.
- *Suture.*—Usually pronounced from stem to blossom end, slightly shallower near blossom end, terminating at blossom end.
- *Cavity.*—From rounded to somewhat elongated in suture plane, from about three-sixteenths to one-fourth inch.
- *Base.*—Rounded.
- *Apex.*—Rounded, pistil point slightly depressed.
- *Stem.*—Length approximately one-fourth inch. Caliper approximately five thirty-seconds of an inch.

Skin: Thin, moderately smooth, no tendency to crack; color is from butter yellow, Plate 4A5, to reddish-orange, Plate 7B8, reddish-orange. Down—scant, very short.

Flesh:
- *Color.*—Plate 4B7 to Plate 5B8.
- *Color of pit well.*—Reddish-orange, 7B7.
- *Flavor.*—Predominantly apricot.
- *Texture.*—Firm, fine, melting.
- *Fibres.*—Medium size, tender.
- *Ripens.*—Fairly even, slightly earlier at apex.
- *Eating quality.*—Good.

Stone:
- *Type.*—Free; adheres to flesh somewhat along ventrical edge.
- *Size.*—Medium to large. Length—from one inch to one and one-quarter inches. Breadth—three-fourths inch to one inch. Thickness—one-half inch to five-eighths inch.
- *Form.*—Ovoid; very slightly cuneate toward apex.
- *Ridges.*—Two ridges extending approximately 180° across the surface of the stone on both sides of the suture plane and approximately 30° displaced from each other.

*Surface.*—Regularly pitted only slightly throughout.
*Color.*—Varies slightly from light brown, Plate 6C5, to brown, Plate 6D6.
*Splitting tendency.*—None.

Use: Canning, drying, shipping, and local market.
*Keeping quality.*—Excellent.
*Shipping quality.*—Excellent.

I claim:

1. A new and distinct variety of apricot tree, substantially as herein shown and described, characterized particularly as to novelty by its large fruit, relatively high red skin color and its early ripening habit in the San Joaquin Valley of Central California.

No references cited.

ROBERT E. BAGWILL, *Primary Examiner.*